(12) United States Patent
Jackels et al.

(10) Patent No.: US 8,590,582 B2
(45) Date of Patent: Nov. 26, 2013

(54) APPARATUS AND METHOD FOR TRANSFERRING PARTICULATE MATERIAL

(75) Inventors: Hans Adolf Jackels, Euskirchen (DE); Harald H. Hundorf, Euskirchen (DE); Siegfried Link, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 308 days.

(21) Appl. No.: 12/958,484

(22) Filed: Dec. 2, 2010

(65) Prior Publication Data

US 2011/0130732 A1    Jun. 2, 2011

(30) Foreign Application Priority Data

Dec. 2, 2009    (EP) ..................................... 09177725

(51) Int. Cl.
*B65B 1/04*    (2006.01)

(52) U.S. Cl.
USPC ................................ 141/81; 141/12; 53/205

(58) Field of Classification Search
USPC .............................. 141/11–12, 71, 81; 53/205
See application file for complete search history.

(56) References Cited

U.S. PATENT DOCUMENTS

| | | | |
|---|---|---|---|
| 4,437,294 A * | 3/1984 | Romagnoli | 53/553 |
| 4,715,918 A | 12/1987 | Lang | |
| 5,562,646 A | 10/1996 | Goldman et al. | |
| 5,607,760 A | 3/1997 | Roe | |
| 5,609,587 A | 3/1997 | Roe | |
| 5,635,191 A | 6/1997 | Roe | |
| 5,643,588 A | 7/1997 | Roe | |
| 5,927,052 A * | 7/1999 | Nippes et al. | 53/445 |
| 6,033,199 A * | 3/2000 | Vonderhaar et al. | 425/81.1 |
| 6,799,409 B2 * | 10/2004 | Altvater et al. | 53/122 |
| 6,805,174 B2 * | 10/2004 | Smith et al. | 141/67 |
| 6,837,281 B2 * | 1/2005 | Spiers et al. | 141/125 |
| 7,093,625 B2 * | 8/2006 | Smith et al. | 141/67 |
| 7,392,636 B2 * | 7/2008 | Conti | 53/433 |
| 7,661,248 B2 * | 2/2010 | Conti | 53/529 |
| 7,849,889 B2 * | 12/2010 | Smith et al. | 141/125 |
| 7,906,065 B1 * | 3/2011 | Brown et al. | 264/511 |
| 8,180,603 B2 * | 5/2012 | Blessing et al. | 703/2 |
| 8,221,672 B2 * | 7/2012 | Brown et al. | 264/511 |
| 8,364,451 B2 * | 1/2013 | Blessing et al. | 703/2 |
| 2003/0034085 A1 * | 2/2003 | Spiers et al. | 141/125 |

(Continued)

FOREIGN PATENT DOCUMENTS

DE        197 54 684 A1    6/1999

OTHER PUBLICATIONS

American Chemical Society publication entitled "Contact Angle, Wettability and Adhesion", Advances in Chemistry Series 43, Chapter 7, edited by Robert F. Gould (Copyright 1964).

(Continued)

*Primary Examiner* — Gregory Huson
*Assistant Examiner* — Nicolas A Arnett
(74) *Attorney, Agent, or Firm* — Charles R. Matson; Andrew A Paul

(57) ABSTRACT

The disclosure concerns an apparatus for transferring, at high speed and in a very effective and accurate manner, particulate material from a feeder into reservoirs of a moving endless surface. The apparatus may include a three-dimensional plate for applying pressure onto the particulate material present between the plate and the moving endless surface. The particulate material is then transferred from the moving endless surface to a substrate.

20 Claims, 7 Drawing Sheets

(56) References Cited

U.S. PATENT DOCUMENTS

| | | | |
|---|---|---|---|
| 2004/0020554 A1* | 2/2004 | Smith et al. | 141/67 |
| 2006/0048880 A1* | 3/2006 | Blessing et al. | 156/60 |
| 2007/0284012 A1* | 12/2007 | Smith et al. | 141/1 |
| 2008/0215166 A1* | 9/2008 | Blessing et al. | 700/31 |
| 2011/0041999 A1* | 2/2011 | Hundorf et al. | 156/276 |
| 2011/0042844 A1* | 2/2011 | Brown et al. | 264/101 |

OTHER PUBLICATIONS

International Search Report, PCT/US2010/058259, mailed Feb. 16, 2011, 7 pages.

* cited by examiner

ND METHOD FOR
APPARATUS AND METHOD FOR
TRANSFERRING PARTICULATE MATERIAL

FIELD OF THE INVENTION

This invention relates to an apparatus for transferring, at high speed and in a very effective and accurate manner, particulate material from a feeder into reservoirs of a moving endless surface, e.g. a drum, by use of a pressure/guiding means, e.g. a specific three-dimensional plate, for applying pressure onto said particulate material present between said plate and said moving endless surface, and guiding said particulate material into said reservoirs, and then transferring the particulate material with said moving endless surface with reservoirs to a substrate; the apparatus and method being in particular useful for the production of absorbent structures for absorbent articles.

BACKGROUND TO THE INVENTION

Traditionally, absorbent articles such as diapers comprise an absorbent core with water-absorbent (cellulose) fibers and particles of superabsorbent polymer particle, also referred to as particles of absorbent gelling material ("AGM"), enclosed by a substrate material, or supported by a substrate material and then closed by a further material, e.g. such as a nonwoven.

Absorbent articles with so-called profiled absorbent cores have been developed, whereby certain regions of the article comprise more AGM than other regions. In such instances, accurate deposition of AGM is important to obtain the required profile. Furthermore, in the case of absorbent cores with only small amounts of, or no, cellulose fibers (having thus AGM particles as the only liquid storage material) accurate AGM distribution is highly important.

Various approaches have been proposed for obtaining absorbent cores with primarily AGM particles and for obtaining absorbent cores that have AGM particles in a specific profile or distribution, such as a predetermined pattern, thickness profile, or adjusting various components of the manufacturing apparatus that act in the machine direction ("MD"), or cross-direction ("CD"). These approaches include indirect printing methods, whereby the AGM particles are taken up by a drum from a bulk storage of AGM particles—said roll or drum having reservoirs on the surface thereof, the number, size and position of which determining the amount and pattern of AGM granules taken up by the drum- and whereby the drum then rotates towards a substrate such as a nonwoven, to then release the AGM onto the substrate (carried by a moving surface).

Surprisingly, the inventors found that such proposed indirect printing processes are in some instances difficult to run at high speed, for example at speeds of more than 800 ppm or more than 1000 ppm (parts (absorbent cores) per minute), in particular when fine particulate material is used and/or when small (and large quantities of) reservoirs are used. It has been found that at high speeds, the AGM particles are not always satisfactorily dropped (e.g. from a feeder/hopper) into the reservoirs of the roll/drum. Reservoirs may only be partially filled, whilst at certain areas of the drum excess AGM may build up. If vacuum (in the roll/drum) is used to aid filling of the reservoirs, then this AGM build-up may obstruct the vacuum suction and this it may further obstruct the filling of the reservoirs This thus may result in an inaccurate distribution of the AGM in the absorbent cores, or even defects in the formed absorbent cores.

The inventors have now found an improved apparatus and method for producing, even at high speed, (absorbent) structures comprising particulate (absorbent) material; said apparatus and method are furthermore able to employ a moving surface (e.g. roll or drum) with a large number of small reservoirs, whilst still delivering accurate filling.

SUMMARY OF THE INVENTION

Aspects of the invention provide an apparatus (1), and method using such apparatus, that includes a particulate material feeder (30) for feeding particulate material to a first moving endless surface (40) (e.g. drum) with reservoirs (50), adjacent to said feeder, and including a means (e.g. three dimensional plate (10)) for guiding said particulate material and applying first and subsequent second pressures on part of said particulate material (100), said first pressure substantially perpendicular to the process direction and subsequently said second pressure being non-perpendicular to the process direction, as described herein, to guide said material into said reservoirs (50); said means or plate (10) being typically connected to a pressure control means.

In a first embodiment the invention relates to an apparatus (1) for making a structure that comprises particulate material (100) supported or enclosed by a substrate material (110), including:

a) a particulate material feeder (30) for feeding particulate material (100) to:
b) a first moving endless surface (40) with a direction of movement (MD) (per surface area of said surface) and with a plurality of reservoirs (50), said surface (40) being adjacent said feeder (30), said first moving endless surface (40) and reservoirs (50) thereof being for receiving said particulate material (100) from said first particulate material feeder (30) and for transferring it directly or indirectly to:
c) a second moving endless surface (200), being said substrate material (110) or being a moving endless surface carrying said substrate material (110), for receiving said particulate material (100) directly or indirectly from said first moving endless surface (40); and
d) a three-dimensional plate (10), for applying pressure on part of said particulate material (100) and for guiding said particulate material (100) into said reservoirs (50), said plate (10) being positioned adjacent said feeder (30) and adjacent said first moving endless surface (40), said plate (10) having a first plate face adjacent said first moving endless surface (40), said plate face having at least:
  i) a first surface area (11) substantially parallel to said first moving endless surface (40), said first area being for (and capable of) applying pressure on said part of said particulate material (100) when present between said first surface area (11) and said first moving endless surface (40);
  ii) a second surface area (12) neighboring said first surface area (11), positioned downstream from the first surface area (11) (in MD), said second surface area (12) being non-parallel to said first moving endless surface (40) and leading from said first surface area (11) towards said first moving endless surface (40), said first surface area (11) and said second surface area (12) are connected to one another, preferably under an angle, including a rounded angle (e.g. curvature, as described herein) or straight angle, and/or said second surface area (12) preferably having an average angle with said first moving endless surface (40) of between 10° and 80°.

In some embodiments herein the plate face has a third surface area (13), neighboring said second surface area (12), being downstream from said second surface area (12) (in MD), said third surface area (13) being substantially parallel to said first moving endless surface (40) and in closer proximity thereto than said first surface area (11), The invention also relates to a method for making a structure that comprises particulate material (100) supported or enclosed by a substrate material (110), including the steps of
a) feeding a first particulate material (100) with a feeder (30) to a first moving endless surface (40) with a plurality of reservoirs (50), adjacent said feeder (30);
b) allowing flow of said particulate material (100), or part thereof, into a volume space present between said first moving endless surface (40) and a three-dimensional plate (10), adjacent said feeder (30) and adjacent and opposing said first moving endless surface (40); and contacting a part of said particulate material (100) with said three dimensional plate (10), said plate having a first plate face adjacent said first moving endless surface (40), and said plate face having:
  i) a first surface area (11) substantially parallel to said first moving endless surface (40); and;
  ii) a second surface area (12) neighboring said first surface area (11), being downstream (in MD) from said first surface area (11), said second surface area (12) being non-parallel to said first moving endless surface (40) and leading from said first surface area (11) towards said first moving endless surface (40), said first surface area (11) and said second surface area (12) are connected to one another, e.g. under an angle, including a rounded angle (i.e. curvature) or a straight angle; preferably said second surface area (12) having an average angle with said first moving endless surface (40) of between 10° and 80°.
c) applying a pressure with said plate onto at least a portion of said particulate material (100) present between said first plate face and said first moving endless surface (40), guiding (or optionally forcing or pressurizing or pushing), said material into said reservoirs (50);
d) transferring said particulate material (100) in said reservoirs (50) of said first moving endless surface (40) directly or indirectly to a second moving endless surface (200), being, or carrying, said substrate material (110);
e) depositing said particulate material (100) onto said substrate material (110).

Each of said first and second surface area have, in some embodiments, an (average) length dimension (in MD) of at least 2 mm; and/or a certain length in MD relative to the distance between centre points of neighbouring reservoirs, as described below.

Said pressure application step c) includes, in some embodiments herein, preferably: firstly applying a pressure, with said first surface area (11) of said plate (10), said pressure being substantially perpendicular to the direction of movement of the first moving endless surface (MD), thereby guiding, or optionally pushing, at least a first portion of said particulate material (100) into said reservoirs (50); and secondly, applying a pressure with said plate face's second surface area (12)s aid pressure being non-perpendicular to the direction of movement of the first moving endless surface (MD), thereby guiding, or optionally pushing, at least a second portion of said particulate material (100) into said reservoirs (50).

The first moving endless surface (40) has for example a surface speed of at least 4.5 m/s, or at least 6.0 m/s, or at least 7.0 m/s, or at least 9.0 m/s.

Said particulate material (100) may have for example a mass median particle size of from 150, or from 200 microns, to 1000 or to 900 microns, or from 300, to 800 or to 700 microns. It may be particulate absorbent polymeric material, as described herein.

The reservoirs (50) may for example have a maximum depth (perpendicular to MD) of from 1.0 to 8.0 mm, or from 1.5 mm to 5.0 mm or to 3.0 mm (herein referred to as average maximum depth: maximum per reservoir, and averaged overall all reservoirs (50), as further described below). The reservoirs (50) may for example have an average maximum dimension (e.g. diameter) in MD (averaged over all reservoirs (50), maximum per reservoir) of up to 20 mm, or up to 10 mm, or up to 6 mm.

In a further embodiment herein, the invention provides an apparatus (1) for making a structure that comprises particulate material (100) supported or enclosed by a substrate material (110), including:
a) a particulate material feeder (30), said feeder (30) being for feeding particulate material (100) to:
b) a first moving endless surface (40) with a direction of movement (MD) (per surface area of said surface, as defined herein) and with a plurality of reservoirs (50), said surface (40) being adjacent said feeder (30), said first moving endless surface (40) and reservoirs (50) thereof being for receiving said particulate material (100) from said first particulate material (100) feeder (30) and for transferring it directly or indirectly to:
c) a second moving endless surface (200), being said substrate material (110) or being a moving endless surface carrying said substrate material (110), for receiving said particulate material (100) directly or indirectly from said first moving endless surface (40); and
d) a first pressure means being positioned adjacent said first moving endless surface (40), for applying pressure on at least part of said particulate material (100) and optionally on part of said first moving endless surface (40), said pressure being in a direction substantially perpendicular to the direction of movement of said moving endless surface (MD) (per surface area where said pressure is applied);
e) a second pressure means adjacent said first moving endless surface (40) and adjacent said first pressure means, for applying pressure on at least part of said particulate material (100), said pressure (in an area) being in a direction non-perpendicular to the direction of movement of said moving endless surface (MD) in said area.

The invention also provides absorbent structures obtainable by the method or with the apparatus (1) of the invention, as described herein.

DETAILED DESCRIPTION OF THE INVENTION

Particulate Material

Figure 1:
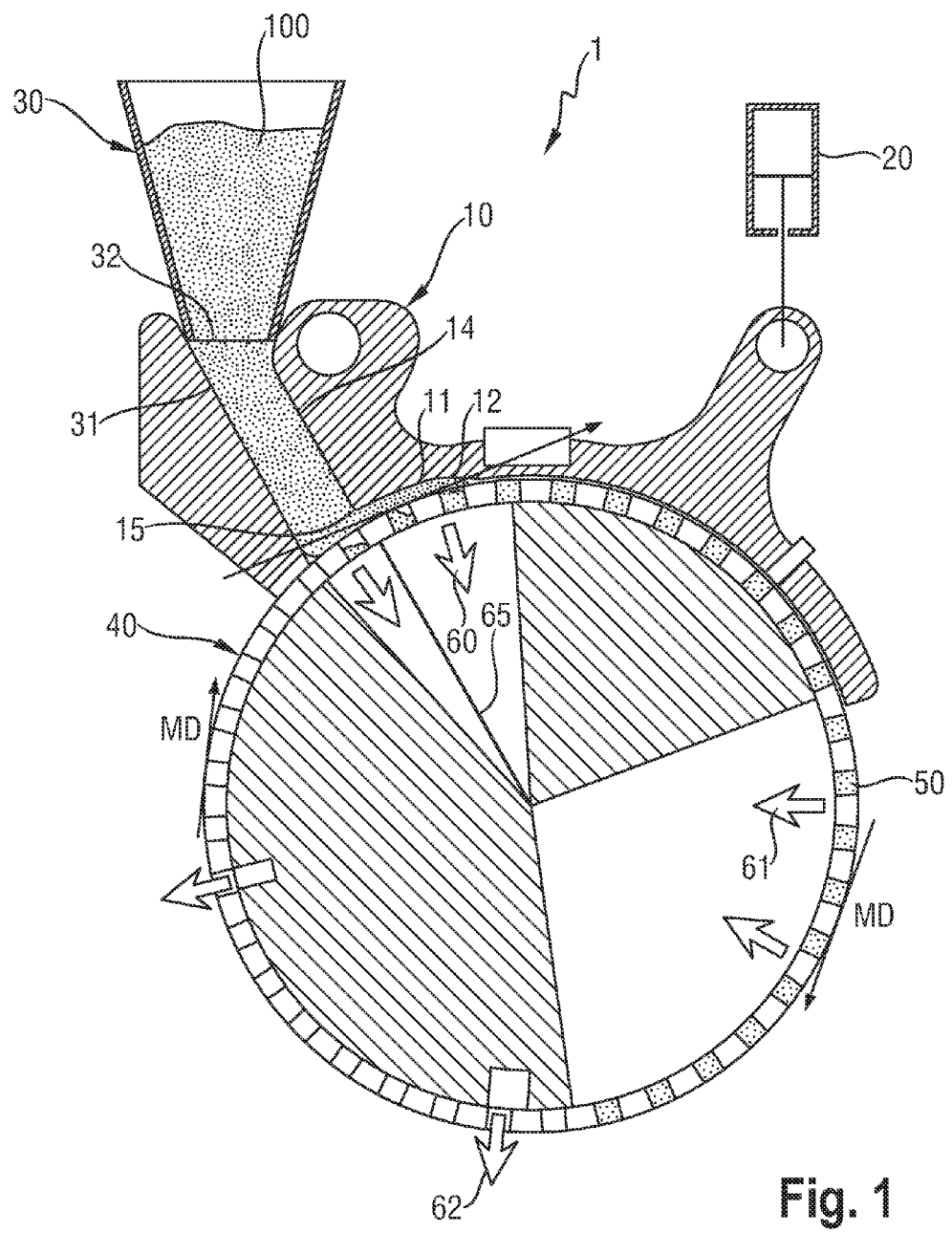
FIG. 1 shows a cross sectional (cross section taken along MD and along the direction perpendicular thereto; e.g. side view) view of a portion of an exemplary apparatus (1) of the invention.

The particulate material (100) herein may be any material in particulate form, e.g. flowable in dry state, which includes particles, flakes, fibers, spheres, agglomerated particles and other forms known in the art.

In some embodiments herein, the particulate material (100) is particulate absorbent (or: superabsorbent) material, and this material is typically polymeric, and also known as particulate absorbent gelling material, herein referred to as AGM. This refers to polymeric materials in particulate form that can absorb at least 10 times their weight of a 0.9% saline solution, i.e. having a CRC value of at least 10 g/g as measured using the Centrifuge Retention Capacity test of EDANA (European Disposables and Nonwovens Association), test method No. 441.2-02 "Centrifuge retention capacity". The particulate AGM herein may have a high sorption capacity, e.g. having a CRC of for example at least 20 g/g, or at 30 g/g. Upper limits may for example be up to 150 g/g, or up to 100 g/g.

The particulate AGM may have a good permeability for liquid, for example, having a SFC value of at least $10\times10^{-7}$ $cm^3$ s/g; or preferably at least $30\times10^{-7}$ $cm^3$.s/g, or at least $50\times10^{-7}$ $cm^3$s/g $10\times10^{-7}$ $cm^3$s/g, or possibly permeability SFC value of at least $100\times10^{-7}$ $cm^3$s/g, or at least a SFC of $120\times10^{-7}$ $cm^3$sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or up to 250 ($\times10^{-7}$ $cm^3$. s/g).

In some embodiments herein the polymers of said AGM are internally cross-linked and/or surface crosslinked polymers.

In some embodiments herein, the aprticualte material herein is absorbent material comprising or consisting of particles of polyacrylic acids/polyacrylate polymers, for example having a neutralization degree of from 60% to 90%, or about 75%, having for example sodium counter ions, as known in the art, e.g. surface crosslinked and/or internally crosslinked and/or post-crosslinked polyacrylic acid/polyacrylate polymers.

In some embodiments herein, the particulate material (100) is in the form of particles with, a mass medium particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0691133. In some embodiments of the invention, the particulate material (100) is in the form of particles whereof at least 80% by weight are particles of a size between 50 µm and 1200 µm and having a mass median particle size between any of the range combinations above. In addition, or in another embodiment of the invention, said particles are essentially spherical. In yet another or additional embodiment of the invention the particulate material (100) has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

The particulate material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate AGM herein may be particles of AGM that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Substrate

The (e.g. absorbent) structure producible with the apparatus (1) and method of the invention comprises a substrate, to receive the particulate material (100). This substrate may be any sheet or web material, in particular paper, films, wovens or nonwovens.

In some embodiments herein, the substrate is a nonwoven, e.g. a nonwoven web; nonwoven, when used herein, refers to a manufactured sheet or web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The substrate herein may be air-permeable. Films useful herein may therefore comprise micro pores. Nonwovens herein may for example be air permeable. The substrate may have for example an air-permeability of from 40 or from 50, to 300 or to 200 $m^3/(m^2 \times min)$, as determined by EDANA method 140-1-99 (125 Pa, 38.3 $cm^2$). The substrate may alternatively have a lower air-permeability, e.g. being non-air-permeable, to for example be better detained on a moving surface comprising vacuum.

In preferred executions, the substrate is a nonwoven material, a nonwoven web, for example of the SMS or SMMS type, and it may have a CD-extensibility or a MD-extensibility, for example of more the 20%, or for example more than 100%, but for example not more than 200%. The ratio of MD-extensibility to the CD-extensibility is at a given load not more than one to two.

Further exemplary absorbent structures and cores are described herein below.

Apparatus

The apparatus (1) of the invention comprises at least the following components: a feeder (30) for feeding particulate material (100) to a moving endless surface with reservoirs (50); said moving endless surface with reservoirs (50), for receiving said particulate material (100) and transferring it to a substrate; a three-dimensional plate (10) adjacent said surface and adjacent said feeder (30); and a support, typically a second moving endless surface (110, 200), for carrying or transporting a substrate, for receiving said particulate material (100) from said first moving endless surface (40) with reservoirs (50).

An exemplary apparatus (1) is shown in FIG. 1, showing the feeder (30), first moving endless surface (40) with reservoirs (50), and a second moving endless surface (200), e.g. substrate (110), or a substrate that may be supported on a second moving endless surface (200), whereby said first moving endless surface (40) rotates and thereby transfers the particulate material (100) from the meeting point adjacent the feeder (30) towards a transfer point where the particulate material (100) is transferred to said substrate.

The apparatus (1) may comprise additional components or modules, upstream and/or downstream from the feeder (30) and first moving endless surface (40). Each of these components, and optional additional components, are now described in detail Feeder (30)

The feeder (30) herein is capable of holding the particulate material (100), typically in bulk quantities, and letting it flow to said first moving endless surface (40). The point or area where the particulate material (100) leaves the feeder (30) is herein referred to as meeting point or area.

The feeder (30) may have any form or shape. The feeder (30) may have a container portion, to hold the particulate material (100), e.g. having a volume of at least 1000 $cm^3$, and a guiding portion, e.g. a pipe-shapes portion, having one or more walls (31) that guides the particulate material (100) from the container portion to the moving endless surface. In some embodiments it has a funnel shape, as shown for example in FIG. 1, having a container portion and a pipe-shaped portion.

The wall(s) (31) of the guiding portion maybe a unitary with the container portion, or a separate portion, connected to the container portion.

In some embodiments, as exemplified as well in the figures, the three-dimensional plate (10) described herein after, has a second plate face (14) with fourth surface area that forms a guide wall for the particulate material (100), and it opposes a wall (31) from the feeder (30).

The feeder (30) has an opening (32), for allowing exit of said material towards the moving endless surface, said opening (32) having opening edges positioned adjacent the first moving endless surface (40), and typically in proximity thereto. In some embodiments, as also exemplified in FIGS. 1 and 2, the opening (32) of the feeder (30) may be taken to be the opening (32) of the pipe-shaped portion of the feeder (30), positioned adjacent (e.g. above) the first moving endless surface (40).

The average distance between said opening edges and said first moving endless surface (40) may be for example less than 10 cm, or less than 5 cm, and it may for example be less than 2 cm or less than 1 cm, and for example at least 0.1 mm, or at least 1 mm.

The opening (32) may have any form, including circular or oval; in some embodiments, the opening (32) is rectangular.

Figure 2:
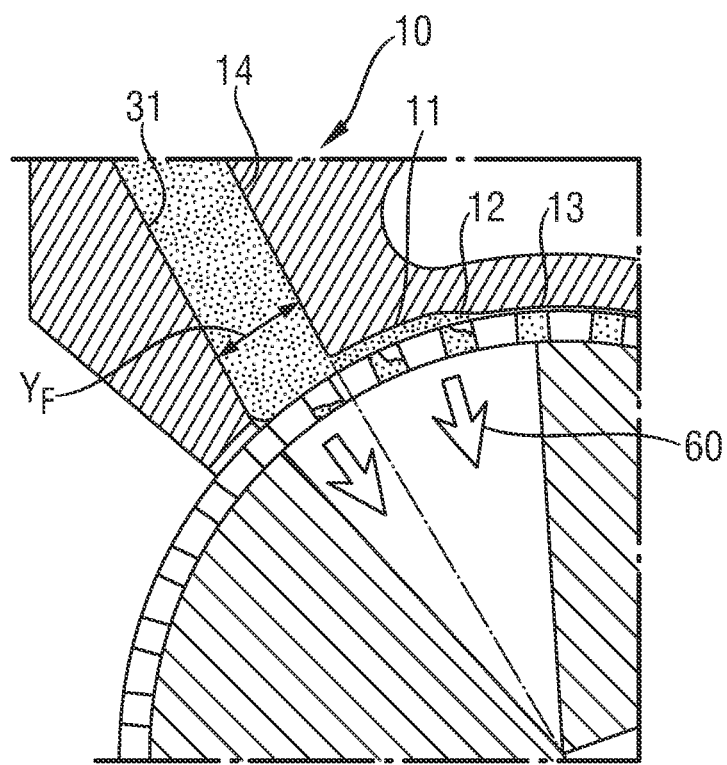
FIG. 2 shows cross sectional (as above) view of a part of the apparatus (1) as shown in FIG. 1, showing an exemplary plate (10) and its plate faces.

The guiding portion and/or the opening (32) of the feeder may have an average dimension in direction of movement (MD), indicated in FIG. 2 as Yf, of for example at the most 140 mm, or for example at the most 80 mm or at the most 60 mm; and typically for some embodiments of the invention related to specific preferred particle size particulate material (100) specified above, at least 10 mm.

In the direction perpendicular to the direction of movement, the opening (32) may have an average dimension about at least 60% of to the width of the first moving endless surface (40), or about equal to said width.

Figure 5:
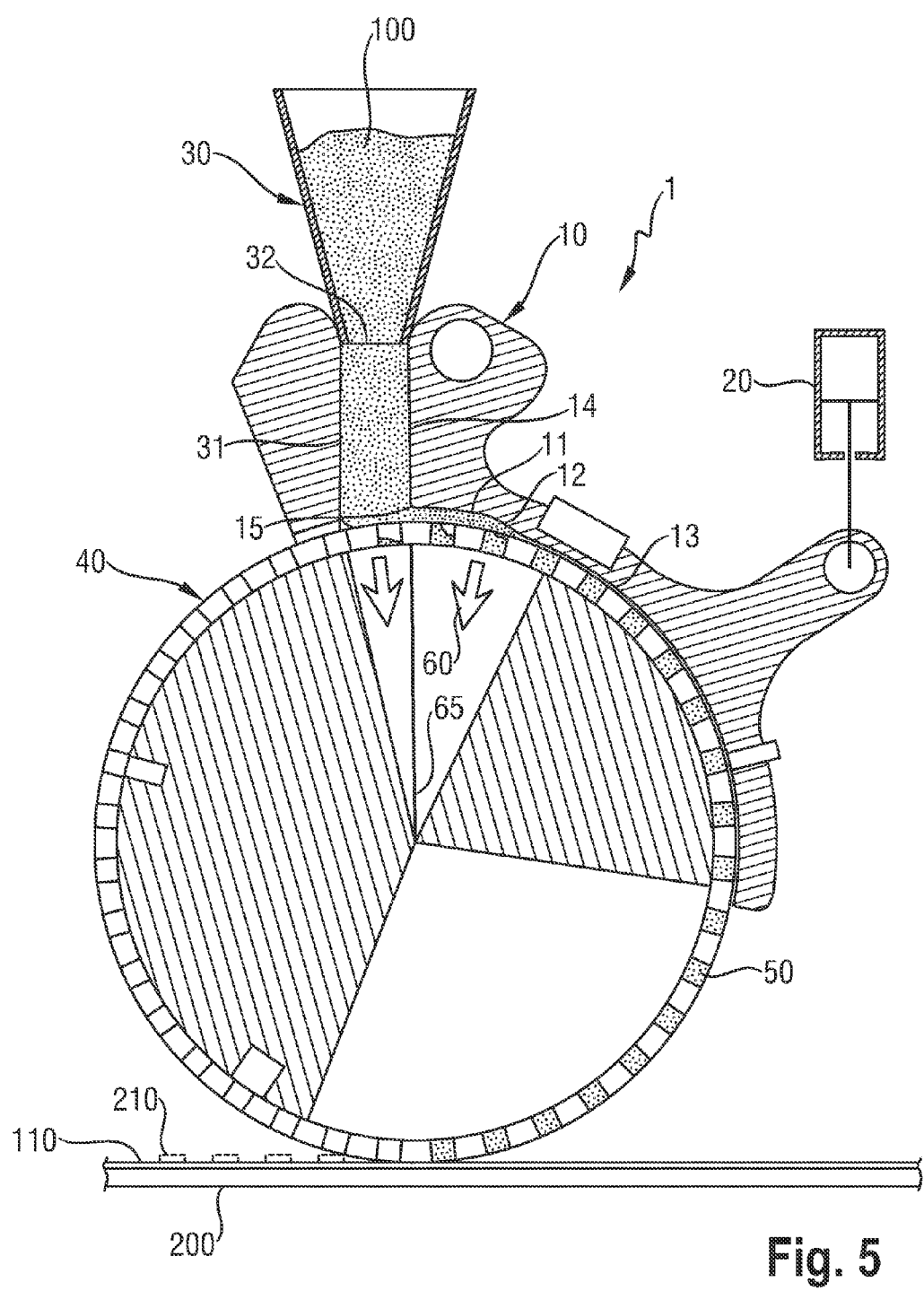
FIG. 5 shows a cross sectional view of a further apparatus (1) of the invention (cross section taken along MD and along the direction perpendicular thereto, e.g. along the line of gravity).

In some embodiments, the feeder (30) is positioned above said first moving endless surface (40), for allowing gravity to help to "feed" said particulate material (100) to said first moving endless surface (40). Hereto, an opening edge of the feeder (30) may be positioned exactly above the first moving endless surface (40) (0°), or, when the first moving endless surface (40) is curved, or even for example circular, as shown in the figures, it may be positioned above said surface, which means at any position between 90° and −90° (e.g. between 9 o'clock and 3 o'clock position), or in some embodiments between 60° and −60°, or between 30° and −30° (measured as angle between an distal edge of the opening (32) and the force line of gravity). FIG. 5 shows for example a feeder (30) positioned exactly above the first moving endless surface (40), whilst FIG. 1 shows a feeder (30) positioned at 30° position (11 o'clock position).

In some embodiments, the side wall or walls (31) are (substantially) parallel to the force line of gravity, so that said particulate material (100) can flow freely to said first moving endless surface (40). This is for example shown in FIG. 5.

In some embodiments, as shown in all Figures except FIG. 3, the feeder's container portion is in contact with or close proximity with the plate (10), and said plate (10) (e.g. the plate's second plate face, with fourth surface area (14), as described herein after), forms a guiding wall (31) for the particulate material (100), together with the wall(s) (31) of (the guiding portion of) the feeder (30). Thus, said particulate material (100) may also fall along and typically in contact with a surface (e.g. the second plate face or fourth surface area (14)) of said plate (10), described herein after. In this case, the opening (and Y f) is defined by the edge of the guiding means wall (31) and the edge of the plate's second plate face.

In another embodiment, said feeder (e.g. guiding portion) may have a wall (31) that is in contact with a surface of the plate (10), e.g. with said second plate face with said fourth surface area (14), described herein after; in some embodiments, the feeder (30) has then also a side wall (31) in contact with and parallel to the plate's fourth surface area (14); such a feeder (30) and plate (10) arrangement is for example shown in FIG. 3. Said side wall may be (substantially) perpendicular to the direction of movement (MD) of said surface (in the point of said first moving endless surface (40) that is adjacent said wall).

First Moving Endless Surface (40)

The first moving endless surface (40) herein may be any moving surface that can rotate to provide a moving endless surface, for example it may be a transporter belt or a cylinder or drum or print roll, as known in the art, which can rotate and thus provide an endless surface.

The first moving endless surface (40) has a direction of movement of said surface, herein referred to as MD. "Direction of movement (MD)" of said first moving endless surface (40), is herein to be taken to be the direction of movement in a certain point of said surface or the average direction of movement in a certain specified area of said surface, as specified herein. Thus, for a curved, e.g. circular, first moving endless surface (40), the direction of movement in a certain point of the surface, or the average direction of movement of a certain area of said surface, is herein determined by determining the tangent in said point or the average tangent of an area (then, said tangent being the average direction of movement in said area). This is for example shown in FIGS. 7 and 8. Said tangent is, as shown, perpendicular to the radius of curvature in said point or perpendicular to the average radius in said surface area, respectively.

The first moving endless surface (40) is typically a rotating device with a certain radius, such as a cylinder or drum, as for example shown in the Figures. The radius of the first moving endless surface (40) may depend on what structure is produced, and what size of structure is produced, and for example how many structures are produced per cycle of the first moving endless surface (40), e.g. drum. For example, the drum may have a radius (65) of at least 40 mm, or of at least 50 mm; it may be for example up to 300 mm, or up to 200 mm.

The first moving endless surface (40) may have any suitable width, but for example a width (perpendicular to MD) corresponding (substantially) to the width of the structure to be produced; this for example be at least 40 mm, or at least 60 mm, or for example up to 400 mm, or up to 200 mm.

It may be useful that the first moving endless surface (40) has opposing lateral zones and a central zone therein between, along the whole surface in MD, and said reservoirs (50) are only present in said central zone. Then, the width dimensions of the surface may apply to the width of the central zone instead.

It should be understood that for purpose of determination of properties of the first moving endless surface (40), such as the MD, the radius, the width of said first moving endless surface (40), the surface area where no reservoirs (50) are present (the area between reservoirs (50)) is used for such determinations. This surface area between reservoirs (50) is herein referred to as "outer surface area" of said first moving endless surface (40). Thus, in some embodiments, the first moving endless surface (40) is a drum with a surface with reservoirs (50), said reservoirs (50) protruding into said drum, and being surrounded by said outer surface area.

The reservoirs (50) may have any dimensions and shape, including cubical, rectangular, cylindrical, semi-spherical, conical, or any other shape. The first moving endless surface (40) comprises reservoirs (50) with a void volume that can be filled with particulate material (100). This may be any suitable number of reservoirs, but for example at least 20 or at least 50.

The reservoirs (50) may be present as identical reservoirs (50), or they may vary in dimension(s) or shape. They may be present in a pattern over the surface of said first moving endless surface (40), or they may be present uniformly over said surface. The exact reservoir (50) pattern, dimensions etc. will depend on the required structure to be formed, but may for example also depend on the particle size of the particulate material (100), process speed etc. In some embodiments at least 30% of the surface area of the first moving endless surface (40) or of said central zone thereof, described above, comprises said reservoirs (50), preferably at least 40% or at least 50%.

The reservoirs (50) may be present as lines of reservoirs (50) in MD and rows in CD, (the direction perpendicular to MD). Alternatively, they reservoirs (50) may for example be present in so-called alternating rows and/or lines (whereby alternating reservoirs (50) form a row and/or line).

The distance in MD between the centre point of a reservoir (50) (said centre point being in the plane of the outer surface of the first moving endless surface (40)) and the centre point of a neighboring reservoir (50) (in a line of reservoirs (50)) may for example be at least 3 mm, or at least 4 mm, or at least 6 mm, or for example up to 40 mm or up to 30 mm or up to 20 mm. This may apply to all such distances between neighboring reservoirs (50) in MD, or this may be an average over all such distances.

The distance in CD between the centre point of a reservoir (50) (said centre point being in the plane of the outer surface of the first moving endless surface (40)) and the centre point of a neighboring reservoir (50) (in a row of reservoirs (50)) may for example also be as above.

Said lines may extend substantially parallel to, and equally spaced from, one another and/or said lines may extend substantially parallel to, and equally spaced from, one another.

In some embodiments, the MD dimension of a reservoir (50) may be (on average over all reservoirs (50) and/or for each reservoir; measured over the outer surface of the first moving endless surface (40)) at least 1 mm, or at least 2 mm, or at least 4 mm, and for example at the most 20 mm or at the most 15 mm. The CD dimension may be within the same ranges as above, or it may even be the same as the MD dimensions for one or more or each reservoir.

The reservoirs (50) may have any suitable dept dimension, and it may depend for example on the height of the first moving endless surface (40) (e.g. radius), the thickness/caliper of the desired structure to be produced, the particle size of the material, etc. The maximum depth of a reservoir (50) and/or of all reservoirs (50), and/or the average maximum depth (average over all maximum depths of all reservoirs (50)) may for example be at least 1 mm, or at least 1.5 mm, or for example 2 mm or more, and for example up to 20 mm, or up to 15 mm, or in some embodiment herein, up to 10 mm, or to 5 mm or to 4 mm or to mm.

According to some embodiments herein, the reservoirs (50) may have a dimension in MD (average; and/or all reservoirs (50)) of from 2 to 8 mm or from 3 mm to 7 mm; and the reservoirs (50) may have a maximum depth and/or average maximum depth of for example from 1.5 mm to 4 mm, or to 3 mm.

The first moving endless surface (40) is adjacent the feeder (30) and adjacent the plate (10) and preferably adjacent said substrate, as described herein. It rotates such that it passes the feeder (30), to receive the particulate material (100) in its reservoirs (50), in a meeting point or area, to then carry said particulate material (100) ("downstream") to a transfer point or area, where the particulate material (100) leaves said first moving endless surface (40), in some embodiments, directly to or towards said second moving endless surface (110, 200); said second moving endless surface (200) may be a moving substrate (110) or a substrate (110) on a moving support.

One possibility to hold the particulate material (100) in the reservoirs (50) may be a vacuum (60) applied to the inner side of the first moving endless surface (40), e.g. drum, in combination with suction holes in (the bottom) of the reservoirs (50), to thus apply the vacuum suction onto the particulate material. The vacuum suction is for example exemplified with the arrows (60) and (61) in the Figures. The vacuum (60, 61) is for example released just before or at the transfer point, e.g. the point where the first moving endless surface (40) is adjacent and opposing said second moving endless surface (110, 200) (as shown with arrow 62). The vacuum (60) may be any vacuum pressure such as for example at least 10 kPa, or at least 20 kPa.

The vacuum (60) may be provided by providing a plurality of vacuum chambers in said first moving endless surface (40) (e.g. in its interior), where vacuum (60) can be applied or released (e.g. indicated by arrow (62)) (connected or disconnected), depending on the position thereof in the process, e.g. when the vacuum chamber reaches the transfer point, the vacuum may be disconnected (62) and the particles can flow from the surface to the substrate, whilst when said chamber reaches the meeting point where the particulate material (100) flows from the feeder (30) to the reservoirs (50), the vacuum (60) is applied (connected).

Additional air pressure may be applied to said particulate material (100) close to or at the transfer point, to ensure that the material flows from the reservoir (50) to the second moving endless surface (110, 200).

In some embodiments, further described below, the plate (10) face adjacent the first endless moving surface has a third surface area (13) in close proximity to and substantially parallel to said first moving endless surface (40), that aids the retention of the particulate material (100) in said reservoirs (50), since it serves as a "cover" of said reservoirs (50). Thereto, said third surface area (13) may be large, as described below, in order to retain said particulate material in said reservoirs (50) up to or close to said transfer point. This is for example exemplified in FIGS. 7 and 8.

Three-Dimensional Plate

The present invention provides improved reservoir (50) filling by use of specific pressure means. In some embodiments of the invention, a three dimensional plate (10) is therefore employed, said plate (10) being positioned downstream from the meeting point/area, and being present adjacent said feeder (30) and adjacent said first moving endless surface (40). Thus, the feeder (30) is positioned before the plate (10), in direction of the process, e.g. in the direction of movement of the first moving endless surface (40) (MD). Thus, it should be understood that at least part of the particulate material (100) contacts the first moving endless surface (40) typically prior to contacting the first surface area (11) of the plate (10).

The plate (10) has a "plate face" which is the surface of said plate (10) adjacent and (substantially) facing said first moving endless surface (40) (opposing it).

The plate (10) face comprises at least a first surface area (11) and second surface area (12) that are connected to one another under an angle, e.g. a "rounded angle", as for example shown in FIGS. 1 and 2, or a straight (true) angle, e.g. with the angle as described below.

In some embodiments, as for example shown in FIGS. 1 and 2, said plate face is a curved side of the plate (10), comprises a first surface area (11), and a second surface area (12), connected to one another with a curvature, herein referred to also as "rounded" angle, with an average "angle", as described herein below; when present, the third surface area (13) may also be connected to the second surface area with a curvature with an average are rounded angle, as described below.

Figure 7:
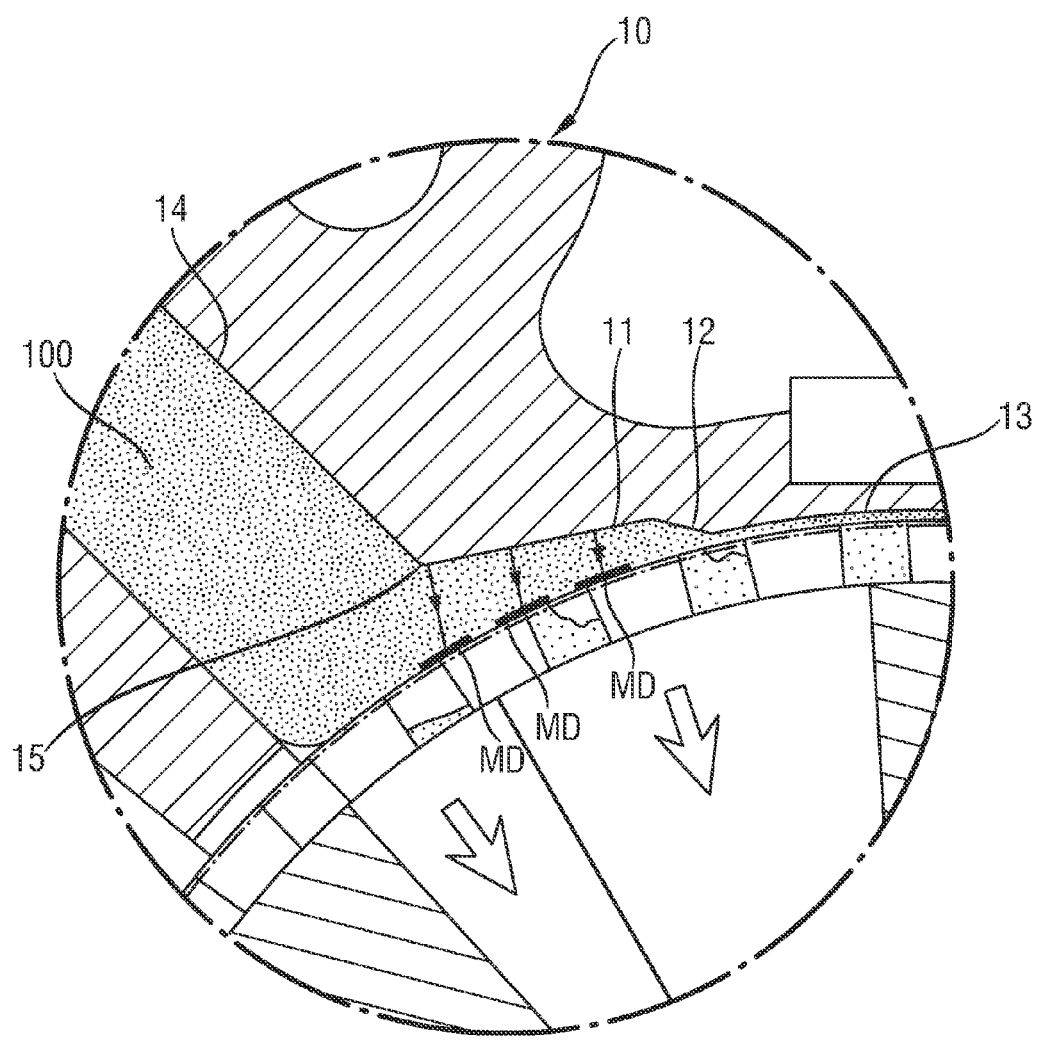
FIG. 7 shows cross sectional view (as above) of an alternative apparatus (1) of the invention with an exemplary plate (10) and its plate faces.

In addition, or alternatively, the plate face may comprise first and second surface areas, connected to one another with an angle, e.g. via an edge with an angle, as for example shown in FIG. 7; and for example a third surface area, for example connected to said second surface area (12) with an edge with an angle, as shown in FIG. 7.

However, in some embodiments it is preferred that the first and second surface areas, and/or when present said second and third surface areas, and/or, when present, said first and fourth surface areas, are (e.g. all) connected with one another under a "rounded angle", e.g. a curvature, so that the connection between the surface areas forms a curvature, as for example shown in FIG. 7.

The plate face comprises a first surface area (11), that is opposed to and adjacent said first moving endless surface (40) and that is substantially parallel to said first moving endless surface (40).

Figure 3:
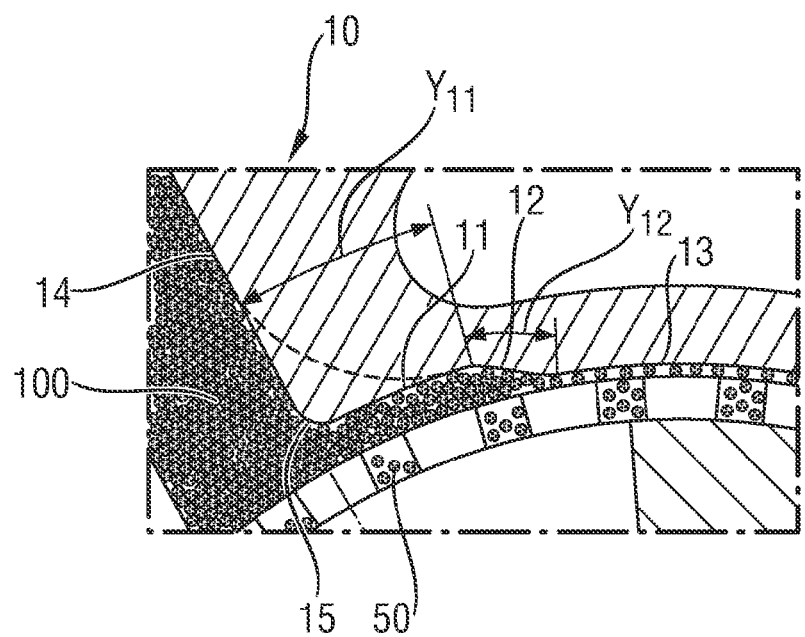
FIG. 3 shows cross sectional (as above) view of an alternative apparatus (1) of the invention with an exemplary plate (10) and its plate faces.
Figure 4:
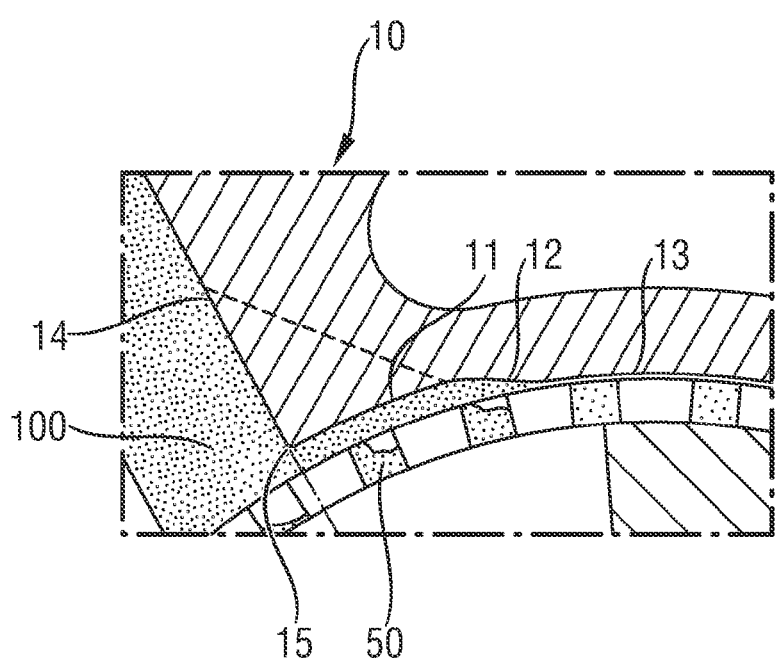
FIG. 4 shows cross sectional (as above) view of an alternative apparatus (1) of the invention with an exemplary plate (10) and its plate faces.

When stated herein that " the first surface area (11) is substantially parallel to the first moving endless surface (40) ", this means that; 1) said first surface area (11) is parallel to the opposing surface area of said first moving endless surface (40) (which is the area where said first surface area (11) overlaps said first moving endless surface (40)), as for example shown in FIGS. 1, 2 and 3; or 2) said first surface area (11) and said opposing surface area of said first moving endless surface (40) are positioned under and average angle of at the most 30° or in some embodiments herein typically at the most 20°, as for example shown in FIG. 7. In the latter case, the first surface area (11) should be positioned such that the edge thereof closest to the feeder (30) (upstream edge) is further removed from the first moving endless surface (40), than the edge connected to the second surface (downstream edge).

Irrespective of whether the first surface area (11) is parallel or substantially parallel to the opposing first moving endless surface (40), in some embodiments, it may be preferred that the first surface area (11) is an even surface, and/or a smooth surface.

In some embodiments, the distance between the first surface area (11) and the opposing area of the first moving endless surface (40) is on average less than 15 or less than 10 times the maximum or mean particle size of the particulate material (100), but at least equal to at least twice or at least four times said mean particle size, and/or at least one or at least twice the maximum particle size. In some embodiments, the average distance may vary depending on the amount of particulate material (100) present under the first surface area (11) of said plate face, as described herein below in more detail. Then, the above average distance may be applicable under a certain pressure, or it may be the average distance at the average operating pressure, for example at 2.5 bar. In some embodiments, the average distance is equal to or more than the (e.g. average) maximum depth of the reservoirs (50), e.g. for example at least 1.2 times or 1.4 or 1.5 times.

Said first surface area (11) of the plate face is in proximity to the first moving endless surface (40), defining a volume between said first surface area (11) and said first moving endless surface (40), wherein during the process particulate material (100) is present. Said first surface area (11) then applies a pressure onto said particulate material (100), or part thereof, to guide (or optionally force, or push) it into said reservoirs (50). Said pressure and direction of pressure perpendicular to first surface area (11) is for example shown by the arrows in FIGS. 7 and 8. In some embodiments herein said pressure applied by said first surface area (11) is substantially perpendicular (as for example shown in FIG. 7) or perpendicular (as for example shown in FIG. 8) to the direction of movement (MD) of said first moving endless surface (40).

When stated herein that the pressure applied by said first surface area (11) of said plate (face) on said particulate material (100) is "substantially perpendicular to the direction of movement" of said first moving endless surface (40), this means herein that the average direction of pressure of said first surface area (11) (taken to be the direction perpendicular to the average first surface area (11) direction) is perpendicular to the average direction of movement of the opposing surface area of said first moving endless surface (40), or that that said average direction of pressure of the first surface area (11) is under an angle of at least 60°, or typically at least 70°, with said average direction of movement of said opposing surface area.

In some embodiments herein, said first surface area (11) may be parallel to said first moving endless surface (40) that it opposes (overlaps); if said first moving endless surface (40) is curved, having a certain radius, e.g. being a drum with a certain radius, the radius of curvature of said first surface are may be about the same, e.g. within 20% or within 10% of one another. In some embodiments herein, the first surface area (11) is curved, having a radius of curvature identical to the radius of curvature of said first moving endless surface (40) (e.g. drum radius).

The plate face may have a width about equal to the width of the first moving endless surface (40), or the central zone thereof.

The first surface area (11) of the plate face may have a length or average length, in MD, of for example at least 2 mm, or at least 4 mm, or at least 6 mm or at least 10 mm.

Alternatively, or in addition the first surface area (11) may have length in MD of at least equal to the dimension of the average distance between the centre points of neighboring reservoirs (50) in MD, as defined herein, preferably at least 1.5 times said dimension of said distance, or at least 2 times said dimension of said distance or at least 2.5 times said dimension of said distance.

Alternatively, or in addition the first surface area (11) may have length in MD that is at least equal to the average reservoir dimension in MD, as defined herein, preferably at least 1.5 times said dimension, or at least 2 times said dimension or at least 2.5 times said dimension or at least 3 times said dimension.

When said first surface area (11) is connected to said second surface area (12) with a curvature, as described above, then said dimension of said first surface area (11) is delimited by the centre line of said curvature, as for example shown in FIG. 3 as $Y_{11}$. The same applies for the dimensions in MD of the second and third and fourth surface area (14), herein after.

The plate face also comprises a second surface area (12) neighboring said first surface area (11), positioned downstream from the first surface area (11) (in MD), said second surface area (12) being non-parallel to said first moving endless surface (40) and leading from said first surface area (11) towards, but in one preferred example not completely to, said first moving endless surface (40), said first surface area (11) and said second surface area (12) are connected under an angle to one another, said second surface area (12) having an average angle with said first moving endless surface (40) of between 10° and 80° (said angle being between said second surface area (12) and said first moving endless surface (40) defining the area where the particulate material (100) is present during the process); in some embodiments the angle is less than 60° or less than 50°. In some embodiments, the angle is at least 20° or at least 30°, or in some embodiments, at least 40°; such larger angle can be seen in FIG. 8.

In one preferred embodiment, the first surface area (11) is parallel to the opposing first moving endless surface (40) and said second surface area (12) is under an angel as defined above.

The second surface area (12) can apply a pressure that is non-perpendicular to the direction of movement of the first moving endless surface (40). When stated herein that the pressure applied by said second surface area (12) of said plate (face) on said particulate material (100) is "a pressure non-perpendicular to the direction of movement of the first moving endless surface (40)", is meant that the average direction of pressure by said second surface area (12) (taken to be the direction perpendicular to the average second surface area (12) direction) is under an angle of less than 60° with the average MD in the area of said first moving endless surface (40) opposing (overlapped) said second surface area. Typically, the average pressure is however not parallel to MD, e.g. said angle is at least 10°.

The second surface area (12) may be a straight or curved surface area. It may be preferred to have a smooth surface.

The second surface area (12) of the plate face may have a length or average length, in MD, of for example at least 2 mm, or at least 4 mm, or at least 6 mm. Alternatively, or in addition the second surface area (12) may have length in MD of at least equal to the dimension of the average distance between the centre points of two neighboring reservoirs (50) in MD, as defined above, preferably at least 1.5 times said dimension of said distance. Alternatively, or in addition the second surface area (12) may have length in MD that is at least equal to the average dimension of a reservoir (50) in MD, as defined herein, preferably at least 1.5 times said dimension.

The first surface area (11) and second surface area (12) are connected under an angle i.e. connected via an edge with a certain angle (as shown in FIG. 7 for example) or connected by a curved area/curvature with an average "angle", as for example shown in all other Figures. For example, the angle or average "angle" between the first and second surface area (12) may be from 100° to 170°; or at least 120° or at least 130°, and preferably less than 160° or less than 150°.

The plate face may have a third surface area, substantially parallel to the first moving endless surface (40), as defined above for the first surface area (11); or, in some embodiments, parallel to said first moving endless surface (40), or under an (average angle of less than 10° or less than 5°.

The third surface area (13) is in close proximity, or optionally partially in contact with, said first moving endless surface (40). In any event the third surface area (13) of the plate face is closer to said first moving endless surface (40) than said first surface area (11) of the plate face.

Figure 8:
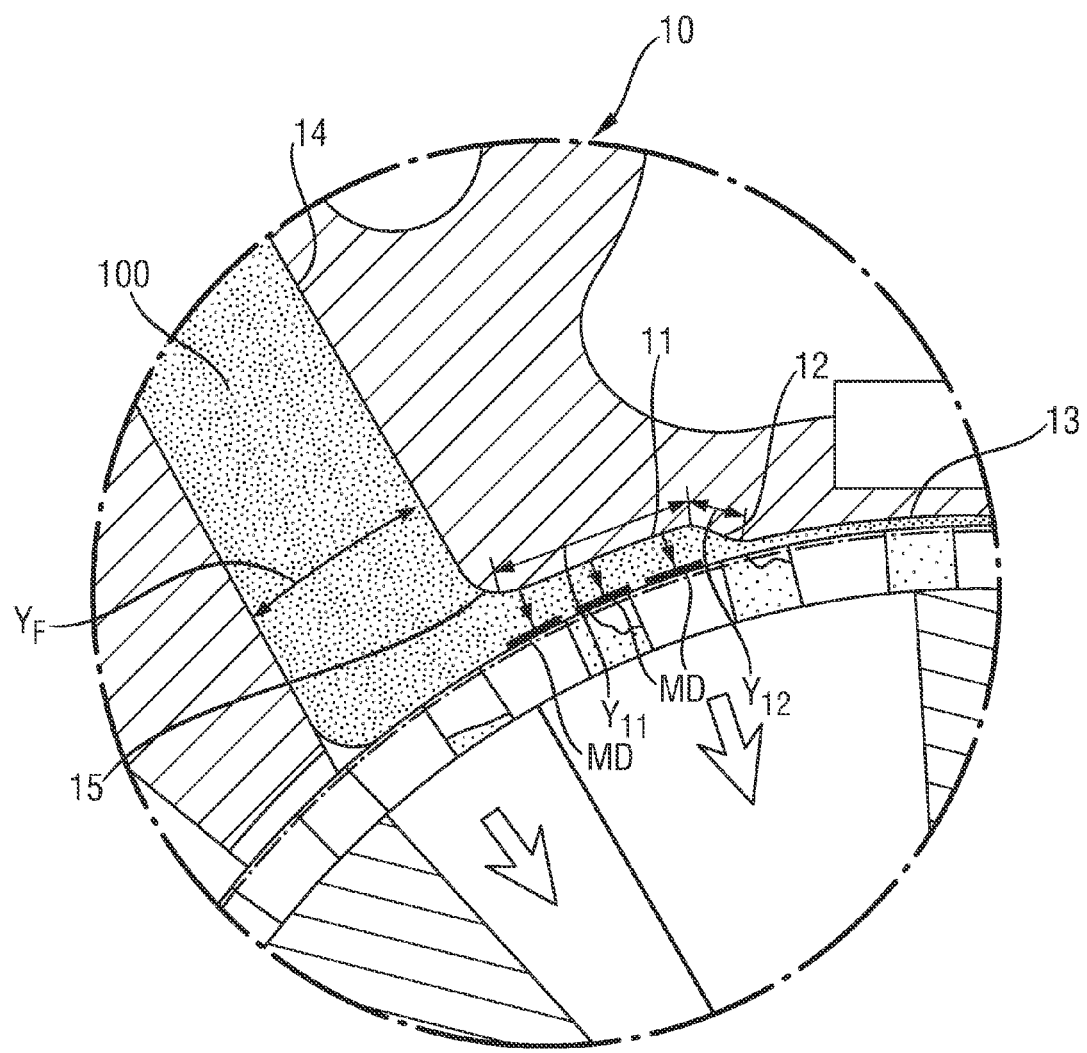
FIG. 8 shows cross sectional view (as above) of an alternative apparatus (1) of the invention with an exemplary plate (10) and its plate faces.

The average distance between the third surface are and the first moving endless surface (40) may be less than a 2 mm, or less than 1 mm; in some embodiments, it may be less than 0.5 mm. Alternatively, or in addition, the average distance may for example be about equal or less than the maximum particle size of the particle material. For example FIG. 8 shows how the third surface area (13) is spaced from the first moving endless surface (40) such that some particulate material (100) may still be present in the space between the third surface are and said first moving endless surface (40), said average distance being for example (slightly) more than or about the mass mean particle size of the particulate material (100).

The third surface area (13) may have a length in (MD) of for example at least 2 mm, or at least 4 mm, or at least 6 mm, or at least 10 mm, or at least 20 mm or at least 30 mm.

As mentioned above, the third surface area (13) may serve as a "closure" for said reservoirs (50), to ensure said particulate material (100) remains in said reservoirs (50). The third surface area (13) may then be for example at least 4 times or at least 8 times or at least 12 times the 9 average) reservoir (50) dimension in MD, and/or of the dimension of the distance between the centre points of two neighboring reservoirs (50) in MD, as above.

The plate is positioned adjacent and downstream of the feeder (30), so that the plate can contact the particulate material (100) directly after release thereof by the feeder (30) (to or towards the first moving endless surface (40)). The position of the plate in the apparatus (1) is thus to a large extend determined by the position of the feeder (30), e.g. by the position of the feeder (30) guiding portion and/or wall(s) (31). In some embodiments, the position of the plate (10) in the apparatus (1) may be such that the outer edge/curvature (15) of the plate face's first surface area (11) is positioned substantially above the first moving endless surface (40), e.g. directly above the feeder (30), or under and angle, as defined herein above, of for example 60° to −90° (3 o'clock) or to −60°, or 30° to −60° or −30°.

The plate may have a second plate face, not opposing the first moving endless surface, that comprises a fourth surface area (14), being adjacent or neighboring or in close proximity or even connected to said feeder (30) (said fourth surface area (14) is thus not part of the plate face comprising said first, second and optional third surface area, but (a part of) another side of the plate (10), e.g. herein referred to as second plate face).

The fourth surface area/second plate face are, typically directly, neighboring and hence connected to said first surface area (11), for example under and angle, or curvature (15) with an average "angle" of for example at least 70° or at least 80°, and up to 110° or 100°, and for example about 90°.

Said second plate face (14) or said fourth surface area (14) may optionally be contacting and guiding said particulate material (100) towards said first moving endless surface (40), as described above.

When the plate (10) is movable during the process, e.g. in responds to changing pressure, the fourth surface area (14) may not be attached to the feeder (30), but only in close proximity thereto.

Figure 6:
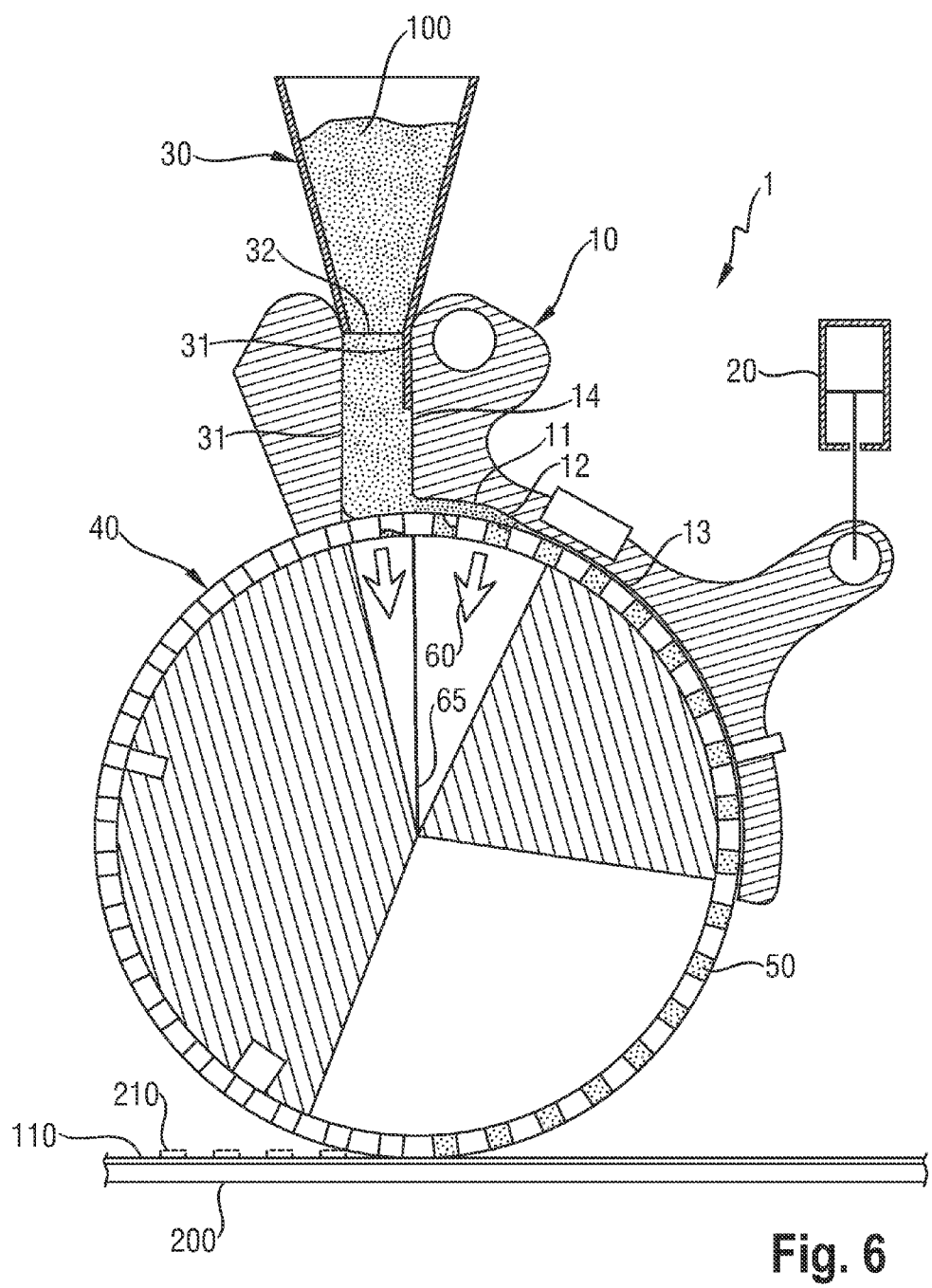
FIG. 6 shows a cross sectional view of a further apparatus (1) of the invention (cross section taken along MD and along the direction perpendicular thereto, e.g. side view).

The fourth surface area (14)/second plate face may be positioned to be an extension to a feeder (30)'s container portion, guiding the particulate material (100) from the container portion towards the first moving endless surface (40), as shown in for example FIGS. 1 and 5. Alternatively, the fourth surface area (14)/second plate face may be positioned to be an extension to a feeder (30)'s guiding portion, e.g. wall (31) and then the particulate material (100) is guided from the container portion towards the first moving endless surface (40) by the feeder wall (31) and then by the fourth surface area (14) of the plate (10), as for example shown in FIG. 6.

The fourth surface area (14)/second plate face may be substantially perpendicular to the direction of movement of the first moving endless surface (40) (MD) under that fourth surface area (14)/second plate face.

The fourth surface area (14) or second plate face may for example have an average height dimension (e.g. substantially perpendicular to the direction of movement of the first moving endless surface (40)) of at least 2 mm, or at least 4 mm, or at least 6 mm, or at least 10 mm or at least 20 mm.

The (external) pressure applied by the plate (10) onto the particulate material (100), e.g. via the first plate face, may be a pressure caused by gravity; the plate (10) may thus for example have a weight of at least 500 grams, or at least 750 grams, preferably at least 1000 grams, and in some embodiments, up to 5000 grams. In such cases, the plate (10) is position above the first moving endless surface (40), as described above. In addition, or alternatively, a pressure application means may be connected to the plate (10) to apply the pressure as described herein.

In some embodiments, the plate (10) applies a certain pressure on to said particles that is controllable, e.g. it can be set to be a constant pressure, or variable over time. This is herein referred to as controlled external pressure. In some embodiments, this pressure is kept substantially constant or in a set range. This pressure range or constant pressure may be for example in the range of, for example, from 1 to 4 bar, or from 1.5 to 3.5 bar or from 1.5 to 3 bar or to 2.5 bar.

In some embodiments, the plate (10) is connected to a pressure control means, said pressure control means (20) being capable of:
  sensing the pressure onto said plate (10) face by said particulate material (100) and
  responding thereto, e.g. by: adjusting the pressure or force of said plate (10) (plate face) onto said particulate material (100).

The pressure control means (20) may include a means to adjust the average distance between the first surface area (11) of the plate face and the first moving endless surface (40), and/or means to change the external pressure.

The pressure control means (20) may be any means know in the art to maintain a certain pressure or adjust a certain pressure, including a hinge, a spring, or in particular an actuator (20).

The actuator (20) may be such that i) it senses the pressure on said plate (10) (face) by said particular material, and in response thereto ii) effects and controls movement of the plate (10) towards or away from said first moving endless surface (40).

Any actuator (20) as known in the art may be used; actuator (20) are typically mechanical, pneumatic, hydraulic or electrical device that performs a mechanical motion in response to an input signal; in the present case, it may be preferred that the pressure onto the plate by the particulate material (100) is the signal to the actuator (20), and that said pressure signal is for example translated into (mechanical) movement of said plate (10).

In some embodiments, the pressure control means (20) is such that when the particulate material (100) exerts a certain too high pressure onto said plate (10), the plate (10) moves away from the first moving endless surface (40), e.g. the distance between said first and second, and optionally third surface area and said first moving endless surface (40) increases. Thereby, the external pressure of the plate (10) may stay substantially constant, e.g. as above.

This helps to avoids that too much particulate material (100) builds up under the plate (10), and/or that the particulate material (100) gets too compacted, to be guided into the cavities, or to be removed from the apparatus (1) as excess material.

Pressure Means:
In some embodiments, the apparatus (1) comprises a first pressure means, e.g. device, being positioned adjacent said first moving endless surface (40), and adjacent or incorporated in said feeder (30), for applying pressure on at least part of, or part of, said particulate material (100), said pressure being in a direction substantially perpendicular to the direction of movement of said moving endless surface (MD), as defined herein below; and in some embodiments, substantially parallel with the direction of gravity.

The apparatus (1) then also typically comprises a second pressure means adjacent said first moving endless surface (40) and adjacent said first pressure means, and positioned downstream there from, for applying pressure on at least part of, or part of, said particulate material (100), said pressure (in an area) being in a direction non-perpendicular to the direction of movement of said moving endless surface (MD), as described below.

Said second pressure means may have a pressure-applying surface substantially non-parallel to the direction of movement of said first moving endless surface (40) (MD), and having for example an average angle with said first moving endless surface (40) of between 10° and 80°.

Said first pressure means may have a pressure-applying surface substantially parallel to the direction of movement of said first moving endless surface (40) (MD), for contacting and applying pressure onto at least part of said particulate material (100) when present between said pressure surface and said first moving endless surface (40).

The properties and specifics of the apparatus (1) and the pressure control means (20) are equally applicable to the present invention regarding the above first and second pressure means. Furthermore, the pressure means may have any of the other properties or specifics specified herein for the plate.

Furthermore, in some embodiments herein, the properties and specifics of the first surface area (11) of the plate (10) equally apply to the first pressure means above, and the properties and specifics of the second surface area (12) of the plate (10) equally apply to said second pressure means.

Second moving endless surface; and optional further apparatus components (units); resulting structures The particulate material (100) is transferred by the first moving endless surface (40) to a second moving endless surface (110, 200). This may be for example a belt or drum, or this may for example be a moving substrate (110), such as a film (e.g. film web) or such as, in some embodiments herein, a nonwoven (e.g. nonwoven web). It may for example be a substrate (110) carried on a moving endless surface such as a belt or a drum. In some embodiments, the second moving endless surface (200) is a web of substrate (110) with another component, such as an adhesive and/or particulate material (100).

The second moving endless surface (110, 200) may have the same surface speed as the first moving endless surface (40), or it may have a different speed. In some embodiments, it has a speed of at least 1000 part per minute and/or a speed of at least 4.5 m/s, or at least 6 m/s, or at least 8 m/s.

The particulate material (100) transfers from the first moving endless surface (40) (i.e. the cavities thereof) to said second moving endless surface (110, 200) in the transfer point or area. The transfer point is the point (e.g. line parallel to the width of the first moving endless surface (40)) where the particulate material (100) starts being released from the cavity and starts being transferred to the second moving endless surface (110, 200). The whole area over which the transfer takes place is herein referred to as transfer area.

In some embodiments herein, the second moving endless surface (200) is a substrate (110) carried on moving endless support, such as a roll, drum or belt. This support may comprise vacuum means and openings, through which the vacuum can be applied to said substrate (110), to retain the substrate on said support.

In some embodiments, the first moving endless surface (40) rotates and the second moving endless surface (110, 200) is for example placed positioned substantially under the first moving endless surface (40) so that the particulate material (100) can transfer in the transfer point or area to said second moving endless surface (110, 200) by gravity. The transfer point may thus be at a parallel to the line of gravity, or under an angel therewith from 60° to −60°, or from 30° to −30°.

The substrate (110) may comprise an adhesive, in order to, at least partially, adhere the particulate material (100) to the substrate (110). In order to better allow vacuum to be applied on the substrate (110) with adhesive, the adhesive may be applied in a pattern, whereby parts of the substrate (110) do not comprise adhesive and parts of the substrate (110) do comprises adhesive. The pattern may correspond to the pattern of the reservoirs (50) of the first moving endless surface (40).

After transfer of the particulate material (100) to the second moving endless surface (110, 200), said surface may move the particulate material (100) to further additional units (which may be part of the apparatus (1) of the present invention), to apply further materials to the particulate material (100) and/or the substrate (110). This may include one or more further adhesive(s), for example applied by a further (downstream) adhesive unit, and/or a further substrate (110), applied for example by a further (downstream) rotating support carrying a further substrate (110), a cutting unit etc.

In some embodiments, the second moving endless surface (200) is a substrate (110) (e.g. on a support) and after transfer of the particulate material (100) to said substrate (110), the substrate (210) moves to a unit that applies an adhesive material, and/or a thermoplastic material and/or an adhesive thermoplastic material, for example in fibrous form, to cover the particulate material (100), or part thereof In another or additional embodiment, the substrate with particulate material (210) moves to a unit that applies a further substrate (110) onto the particulate material (100), or optionally onto said adhesive and/or thermoplastic and/or thermoplastic adhesive material.

Said further substrate (110) may comprise adhesive on the side that contacts the particulate material (100) (or optionally said thermoplastic and/or adhesive and/or thermoplastic adhesive material), to better adhere said substrate (110) to said particulate material (100). In some embodiments, the substrate with particulate material (210) (e.g. as a layer) is moved to a further unit, where a second substrate with particulate material (100) (e.g. as a layer), e.g. made by an apparatus (1) of the invention in the manner described herein, is superposed thereon, for example such that substrate (110) and further substrate sandwich said particulate material (100), e.g. said two particulate material "layers". In some embodiments, the substrate with particulate material (210), made with an apparatus (1) of the invention and the method of the invention, is moved to a further apparatus (1) of the invention, that transfers particulate material (100) onto said substrate with particulate material (210), (optionally onto said thermoplastic and/or adhesive and/or thermoplastic adhesive material).

The apparatus (1) of the invention may thus comprise one or more units, upstream and/or downstream of said first moving endless surface (40), such as adhesive application unit(s), and/or substrate application unit(s). Such adhesive application units may be selected from any type known in the art, in particle slot coating units and spray units.

The resulting substrate with particulate material (210) may thus be a web of structures herein (optionally combined with any of the further materials described above) and it may then move to a cutting unit, that cuts the substrate with particulate material (210), e.g. web of structures, into individual structures, e.g. absorbent cores for absorbent articles, or absorbent articles or partial absorbent articles. Such absorbent cores or partial absorbent articles may then be combined with further absorbent article components, described herein below, to form a final absorbent article.

The support of said substrate (110) may comprise a grid, having for example plurality of bars extending along the direction of movement of said second moving endless surface (110, 200), and extending (substantially) parallel to and (equally) spaced from one another; and/or a plurality of cross bars extending along the direction perpendicular to the direction of movement of said second moving endless surface (110, 200), and extending (substantially) parallel to and (equally) spaced from one another; said cross bars or bars forming thus" channels" between them; or if the cross bars and bars are both present, forming "indentations" between them. The reservoirs (50) of the first moving endless surface (40) may then correspond (in the apparatus/during the transfer process) with the islands or part of the channels and the particulate material (100) may transfer from the reservoirs (50) into said channels or into said indentations. The support grid may be a vented support grid with vacuum means, applying a vacuum between the bars and/or crossbars, and thus in the areas of the substrate (110) supported by the grid, forming the islands or channels.

In some embodiments herein, a coversheet material, in the form of a web material, is placed over the particulate material (100) on said second moving endless surface (110, 200), after transfer, to cover said particulate material (100), and typically to enclose it between said coversheet and said substrate (110).

In some embodiments, the particulate material (100) is placed in a longitudinally (MD) extending portion of the substrate (110), leaving a longitudinal (MD) extending portion free of particulate material (100). Then, the portion free of particulate material (100) may be folded onto said particulate material (100), after transfer thereof, to provide a cover thereof In this embodiment, the substrate (110) is thus also a cover sheet. A further coversheet may be used in addition, as specified above.

The substrate (110) may be joined to itself or to a cover sheet or other component, as described above, by any means, for example by ultrasonic bonding, thermo-bonding or adhesive-bonding, e.g. for example sprayed adhesive bonding. The bonding region between the coversheet and the substrate (110), or may for example be at least 1%, or at least 2%, or for example at least 5%, but for example not more than 50% or no more than 30% of the surface area of the substrate (110). Preferably, the bonding region comprises essentially no particulate material (100).

As mentioned above, a adhesive, and/or thermoplastic or thermoplastic adhesive material may serve to at least partially cover and at least partially immobilize the particulate material (100), for example an adhesive and/or thermoplastic or thermoplastic adhesive material in fibrous form, e.g fibrous layer which is at least partially in contact with the particulate material (100) and optionally partially in contact with the substrate (110). The thermoplastic material may be a hot melt adhesive material. In accordance with certain embodiments, the thermoplastic (adhesive) material may comprise a single thermoplastic polymer or a blend of thermoplastic polymers, having for example a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. The thermoplastic polymer may have a molecular weight (Mw) of more than 10,000 and a glass transition temperature (Tg) usually below room temperature or $-6° C.>Tg<16° C$. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic (adhesive) material may be in the form of fibers of an average thickness of about 1 to about 50 micrometers or about 1 to about 35 micrometers and an average length of about 5 mm to about 50 mm or about 5 mm to about 30 mm.

The cover layer may comprise the same material as the substrate (110), or may comprise a different material. In certain embodiments, suitable materials for the cover layer are the non-woven materials, useful for the substrate (110).

Method

The present invention also relates to a method as described above and as claimed herein. Any of the above described features of the apparatus (1) and functions and method steps thereof apply the method of the invention. In particular, in said method, the pressure application step c) includes for example: firstly applying a pressure, with said first surface area (11) of said plate (10), said pressure being substantially perpendicular to the direction of movement of the first moving endless surface (MD), thereby guiding (or optionally pushing) at least a first portion of said particulate material (100) into said reservoirs (50); and secondly, applying a pressure with said plate face's second surface area (12) said pressure being non-perpendicular to the direction of movement of the first moving endless surface (MD), thereby guiding, or optionally pushing, at least a second portion of said particulate material (100) into said reservoirs (50).

In said method, a third surface area (13) as described above, may guide, or optionally push, a third portion of said particulate material (100) into said reservoirs (50) and/or it may aid retention of said particulate material (100) in said reservoirs (50).

In the method, the pressure may be controlled by use of a pressure control means, including an actuator (20), as described above.

The method and apparatus (1) herein may produce for example at least 1000 part per minute (ppm, or at least 1100 or at least 1200; said "parts" being the individual structures described herein, e.g. for example absorbent structures.

In the method herein, said first moving endless surface (40) may have for example a surface speed of at least 2.0 m/s, or at least 3 m/s or at least 4.5 m/s, or at least 6.0 m/s, or at least 7.0 m/s, or at least 7 m/s. Alternatively, or in addition, the first surface area (11) may have a speed defined by parts per minute, of at least 500 parts per minute, or at least 1000 parts per minute. In one such embodiment, the first moving endless surface (40) is a drum, comprising cavities corresponding to one or two, preferably one (e.g. absorbent) structure herein.

The method herein may be particularly useful to make absorbent structures (including: a web thereof that may then be divided, e.g. cut, into individual absorbent structures), whereby said particulate material (100) is AGM, with a mass median particle size of from 150 to 1000 microns, or from 200 or 300 to 700 microns.

The method may employ the step to add a thermoplastic material, and/or adhesive material and/or thermoplastic adhesive material to said substrate (110) prior to transfer of said particulate material (100) and/or to the said particulate material (100) and/or substrate (110) after said transfer, and/or the step to add further substrate (s) or covering sheet(s) and/or to fold the substrate (110) and close the substrate (110) over said particulate material (100) and/or the step to add a further substrate with particulate material (100) (210), as described above.

Absorbent Cores and Absorbent Articles

The apparatus (1) and method of the invention are for example useful to produce absorbent structures, such as acquisition layers and/or absorbent cores for absorbent articles, or partial absorbent articles, for example the backsheet and core and optionally the topsheet, of such article; and/or to produce absorbent articles.

"Absorbent article" refers to devices that absorb and contain body exudates, and, more specifically, refers to devices that are placed against or in proximity to the body of the wearer to absorb and contain the various exudates discharged from the body. Absorbent articles may include diapers, including fastenable diapers and (refastenable) training pants; adult incontinence undergarments (pads, diapers) feminine hygiene products (sanitary napkins, panty-liners), breast pads, care mats, bibs, wound dressing products, and the like. "Diaper" refers to an absorbent article generally worn by infants and incontinent persons about the lower torso so as to encircle the waist and legs of the wearer and that is specifically adapted to receive and contain urinary and fecal matter. As used herein, the term "body fluids" or "body exudates" includes, but is not limited to, urine, blood, vaginal discharges, breast milk, sweat and fecal matter.

As well known in the art, the absorbent core is the portion of the article that retains absorbed bodily fluids. The absorbent core herein thus comprises the particulate material (100) that is an absorbent particulate material (100) (as defined herein) disposed on a substrate (110), formed by the apparatus (1) and method herein. The absorbent core does not include an acquisition system, a top sheet, or a back sheet of the absorbent article, which are additional components of such absorbent articles. The absorbent core is typically sandwiched between at least a backsheet and a topsheet. The absorbent cores herein may thus comprise typically a further layer, e.g. a further particulate material (100) and substrate layer (110 or 210), coversheet, or a further layer being a portion of the substrate (110) folded over said particulate material (100), as described above. The absorbent core herein may comprise adhesive and/or thermoplastic material, as described above.

In preferred embodiments herein, the absorbent core, and optionally the absorbent article, is "substantially cellulose free" is used herein to describe an absorbent core or article, that contains less than 10% by weight cellulosic fibers, or less than 5% cellulosic fibers, or less than 1% cellulosic fibers, or no cellulosic fibers.

In certain embodiments, the absorbent structure or core herein may comrpsie said particuale absorbent (polymeric) material, e.g. AGM, in an amount greater than about 80% by weight of the structure or absorbent core, or greater than about 85% by weight, or greater than about 90% by weight of the absorbent core, or greater than about 95% by weight of the core.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

It has been found that, for most absorbent articles such as diapers, the liquid discharge occurs predominately in the front half of the diaper. The front half of the absorbent structure herein may thus comprise most of the absorbent capacity of the core. Thus, according to certain embodiments, the front half of said absorbent structure herein may comprise more than about 60% of the particulate material (100), e.g. AGM, or for example more than about 65%, 70%, 75%, 80%, 85%, or 90% of the total amount of particulate material (100), e.g. AGM.

The absorbent article herein may comprise in addition to an absorbent core, a topsheet and backsheet, and for example one or more side flaps or cuffs. The topsheet or cuffs or side flaps may comprise a skin care composition or lotion or powder, known in the art, panels, including those described in U.S. Pat. Nos. 5,607,760; 5,609,587; 5,635,191; 5,643,588.

Preferred absorbent articles herein comprise a topsheet, facing the wearer in use, for example a nonwoven sheet, and/or an apertured sheet, including apertured formed films, as known in the art, and a backsheet, an absorbent core, having optionally a core coversheet facing the wearer in use.

The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind., and sold under the trade names X15306, X10962 and X10964.

The backsheet, or any portion thereof, may be elastically extendable in one or more directions. The backsheet may be attached or joined to a topsheet, the absorbent core, or any other element of the diaper by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent core, and extending longitudinally along said core, and typically being mirror images of one another in the Y-axis (in MD) of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the Y-axis (longitudinal axis; MD axis) of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Preferred fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent core, capable of accepting, and distributing and/or immobilizing bodily exudates. Suitable sublayers include acquisition layers, surge layers and or fecal material storage layers, as known in the art.

Other suitable components of absorbent articles include acquisition layers. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, preferably looped, strands of fibers, or preferably apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

The (absorbent) structure or core formed herein comprises in some embodiments a substrate with said particulate material (210), whereby said substrate (110) is C-folded to enclose said particulate material (100). In other words, the particulate material (100) may be deposited unto the substrate (110) and the substrate (110) may then be folded to cover the particulate material (100). Alternatively, or in addition, a separate sheet material, or cover sheet, may be placed over the particulate material (100) after it is deposited onto said substrate (110), to cover the particulate material (100). Such a coversheet may be any of the material described herein above as substrate (110) material, e.g. a nonwoven sheet or web.

Alternatively, or in addition, two or more of the substrates with particulate material (210) deposited thereon may be produced and placed onto one another, to cover one another. Hereby, an additional coversheet may be placed first onto the particulate material (100) on said substrate, and then a further substrate with particulate material (210) may be placed thereon, typically such that said latter particulate material (100) contacts said coversheet.

Some embodiments of the invention relates to a pack comprising a multitude of at least five absorbent articles, as described below, comprising each an absorbent structure (herein referred to as absorbent core) produced by use of the method of the invention and/or by use of the apparatus of the invention, typically at a line speed as described above. The apparatus and method of the invention are such that very accurate filling of the reservoirs and very accurate transfer is achieved, even at high speed. The resulting absorbent cores, including a web of such cores that is subsequently separated into individual cores, are therefore substantially identical.

Of each of the absorbent article of the multitude of articles, comprises an absorbent core obtained by use of the method or the apparatus (1) of the invention, and each core comprises particulate polyacrylate/polyacrylic acid polymeric material, as described herein above, typically such crosslinked polymers, having internal and/or surface crosslinking. The multitude may of 5 articles, or of course it may be more than five absorbent articles, for example at least 10 absorbent articles. Typically, within a pack, the articles are consecutively produced articles. Thus, in some embodiments, the absorbent cores of said multitude are consecutively produced absorbent cores, produced by the method and/or apparatus of the invention.

The pack may be any pack, of any shape, and made of any packaging material, as known in the art, including a plastic bag, cardboard box etc.

Each absorbent core comprises (in addition to said particulate polymeric material) a nonwoven substrate material (110) and an adhesive material, adhering said particulate polymers to said substrate material and/or to one another, as described herein. In some embodiments, more than one adhesive material may be used. It may comprise more than one substrate material, and/or addition core cover materials, e.g. nonwovens, as described herein above. In some embodiments, the absorbent core may consist of said particulate material, adhesive material(s) and substrate material(s), and optional additional core cover materials.

Each absorbent core has a length dimension (in MD) and a width dimension (CD; perpendicular to the MD direction), each absorbent core is dividable in at least 10 strips extending along the width (in CD) of the core and each strips having a dimension in MD of 1.0 cm; the method below describes how such strips can be obtained from an absorbent core. Each absorbent core has at least 10 such strips and each core has at least 10 such strips that each have an "internal basis weight" of at least 100 gsm, but preferably at least 150 gsm, or preferably at least 200 gsm, said internal basis weight the basis weight of the particulate polyacrylate/polyacrylic acid polymeric material or of said particulate material and adhesive material(s), when present, but excluding said substrate material(s) and additional core cover materials.

For such multitude of absorbent articles, each having such an absorbent core, the average relative standard deviation of the amount of particulate polyacrylate/polyacrylic acid polymeric material is 10% or less, or 7% or less, or 5% or less, or 3% or less; this is the average over 10 relative standard deviations (% RSD, being average/standard deviation*100), each of said 10 being the % RSD of 5 equal strips (as defined below), each of which taken of one of the 5 articles, as defined and determined by the test method below. As set out below, the amount of AGM can be expressed in meq (AGM) or translated into grams (AGM).

This may be equally determined and applicable for multitudes of absorbent articles of more than 5, e.g. 10 or more, as set out below. When more than 5 articles are present, then the above average % RSD applies to at least 5 consecutive articles in the pack, but it may apply to more than 5 articles, or to more sets of 5 consecutive articles, or to all articles in the pack. Packs may in some embodiments comprise up to 100 articles, or up to 75 articles, or up to 50 articles.

The polyacrylic acid/polyacrylate polymeric material (AGM) herein may comprise other ingredients, such as coating agents; in any event, and in some embodiments herein, if such additional agents (e.g. coating agents) comprise acid/base groups, these agents are typically present at a level of less than 1% by weigth of the AGM, and hence neglectable in the determination of the average % RSD. In another embodiment herein, the absorbent core comprises no other compounds that have acid or base croups other than the polyacrylic acid/polyacrylate polymer particles.

Because the method of the invention and the apparatus of the invention produce such cores with very accurate particulate material transfer to the substrate material, no lumps of access material are obtained. Hence reduced amounts of adhesive material may only be needed, for example such that the weight ratio of said particulate polyacrylate/polyacrylic acid polymers to said adhesive material (in said core) is from 15:1, or from 20:1, or from 25:1, to 100:1, or to 40:1 or to 40:1. It should be noted for the purpose of the absorbent articles of the invention, that the adhesive material(s) generally do not comprise any significant amount of acid or base group containing components Separately, or in addition, because the transfer of the particulate material is very accurate, the basis weight of the substrate material may be reduced, for example such that it has a basis weight of 15 gsm or less, or preferably 12 gsm or less, or 10 gsm or less.

The process herein is preferably a high speed process, as described herein; therefore, said absorbent articles comprises typically machine-readable registration marks, for example comprised on said substrate material, and/or on the topsheet, backsheet and/or any other component of said absorbent article. Such registration marks, known in the art, enable exact positioning of components of the a article during the manufacturing process with respect to said registration marks and/or to one another.

The amount of a particulate polymeric material (AGM) per strip and/or per surface area, e.g. the basis weight thereof, may vary along (MD); the absorbent core may be a so-called profiled core, whereby certain strips have a higher (internal or AGM) basis weight than another strip. It may be profiled in thickness direction; and/or the core may also profiled in CD direction, being a shaped core having a width dimension that varies, for example having a smaller width in the centre of the core, than in the average width in the front quarter and/or back quarter of the product.

Method to Determine Average Relative Standard Deviation

In this method, samples containing polyacrylate/polyacrylic acid based polymeric material (herein referred to as AGM) are first reacted with a known amount of HCl. An aliquot of the solution is then titrated to a bromophenol blue indicator with a NaOH solution. The titration results can be expressed as the milliequivalents (meq) of the neutralized acid groups of the AGM.

Of 5 absorbent articles of a multitude of absorbent articles (e.g. 5 or more or 10 or more), the absorbent cores produced by the method/apparatus of the invention are removed.

A first absorbent core is oriented such that the transverse (CD) edge that is in the article towards the front (of the user, e.g. front waist of a diaper) is labeled top, and the opposite transverse end is labeled bottom. The transverse and longitudinal axes are determined (and optionally marked on the core). The absorbent core is then cut in transversely extending (i.e. along full width) strips with an equal dimension in MD of 1.0 cm±0.01 cm; the last strip at the bottom may be less than 1 cm, but in that case disregarded for this test.

A cutting die is used with a hydraulic press to section the core into such strips. The die is manufactured such that it is able to cut strips over the entire length (MD) and width (CD) and thickness of the core. The die is placed on an even surface (work bench) with its cutting blades facing upward, and the core is laid across the die centered along its transverse and longitudinal axes. A 0.25 inch Lexan plate with MD and CD dimensions larger than the die is placed on top of the core and then the assembly is placed in the hydraulic press and cut. The strips remain contained within the die until analysis to ensure that no AGM particles are lost. Each strip is labeled with a consecutive number (1 at top, 2, 3, 4, etc).

Each strip has thus a MD dimension of 1.0 cm, but the strips may have different (average) widths (average per strip). For the purpose of the invention, there are at least 10 strips per core.

For this first absorbent core, the "internal basis weight", as defined above, per strip is determined, by determining for each strip of said first core the surface area of said strip (1.0×CD dimension), and then removing the substrate material(s) (and other core cover materials, if present), as described herein, to obtain only the material(s) inside the absorbent core, i.e. the particulate polyacrylic acid/polyacrylate polymeric material transferred by the process/apparatus of the invention and optional adhesive material(s), if present. The weight of this material(s) is determined per strip, and then the "internal" basis weight per strip can be calculated (being the weight of said polymeric material and optional adhesive material per surface area of the strip).

Then, the 10 strips with highest "internal; basis weight" are determined for said first absorbent core. For the purpose of this test and this invention, there should be at least 10 strips that have an internal basis weight of at least 100 gsm (or preferably at least 150 gsm or at least 200 gsm as described herein above). The other strips (if any) are disregarded for the titration test below.

Said 10 strips are then submitted to the titration, described below. (For example strips 4, 5, 6, 7, 8, 9, 10, 12, 14, and 15.)

The remaining 4 absorbent cores of the remaining (e.g. selected) 4 absorbent articles (of the multitude) are each separately cut with the die exactly as set out above for the first absorbent core. Then, per absorbent core, the same strips as said 10 strips with highest internal basis weight are separately removed from the die and separately submitted to the titration method below. (For example strips 4, 5, 6, 7, 8, 9, 10, 12, 14, and 15, per core). Thus a total of 50 strips are obtained and separately submitted to titration.

Titration Method:

A 50 mL certified digital burette (e.g. Digitrate, Jencons Scientific, Bridgeville, Pa., or equivalent) is used for the titration. 0.1N HCl and 0.1N NaOH solutions are used (Baker Analyzed certified volumetric solutions; J. T. Baker, Phillipsburg, N.J.).

An individual strip is removed from the die placed into a 400 mL beaker and the substrate material(s) and optional other core cover materials are removed, ensure no loss of AGM during this transfer or substrate removal takes place. The remaining sample is herein referred to as "AGM".

Using a Class A volumetric pipet, 250 mL of 0.1N HCl acid is added, the AGM is submerged and soaked with stirring for 30 minutes. Then, this is filtered through a Whatman #4 filter paper into another 350 mL beaker. Using a Class A volumetric pipet, 25 mL aliquot of the filtered solution is pipeted into a 50 mL beaker. Four drops of 1% bromophenol blue indicator (w/w in deionized water) is added, and the solution is titrated with 0.1N NaOH to a blue endpoint. The volume of titrant is recorded to ±0.01 mL.

Each of the strips above (in total 50) is measured in like fashion.

Millequivalents of the neutralized AGM acid groups can be calculated per strip as:

meq (AGM)=2.5 meq (HCl)−[mL 0.1N NaOH*0.1 meq/1 mL]

This value in meq (AGM) can be translated into grams (AGM), as known in the art, if desired Then, the standard deviation over 5 strips of same number (e.g. the strips no. 4 of the 5 cores) can be determined and the relative standard deviation (% RSD, being average/standard deviation*100) between said equal strips (e.g. no. 4) of 5 articles.

This is determined for each set of 5 strips of the same number, to obtain a total of 10 standard deviations and 10 relative standard deviation (e.g. for strips 4, 5, 6, 7, 8, 9, 10, 12, 14, 15).

Then the average of said 10 relative standard deviations (% RSD) is calculated and reported as "average relative standard deviation" (average % RSD), as claimed herein. For the purpose of the invention, this should be 10% or less, but preferably 7% or less, or 5% or less.

The above test may be done for any multitude of absorbent articles of the invention, by taking 5 consecutive articles and cores thereof of a pack; the test may also be done in the same manner as set out above for more than 5 articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood, for the purpose of the invention, that the Figures are not to scale and that furthermore the dimensions of the exemplified apparatus and elements thereof, the dimensions of the particulate material, and said dimensions relative to one another, as depicted in the Figures are not intended to reflect the true dimensions of said elements or particulate material, or relative dimensions thereof, unless stated otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making a structure that comprises particulate material supported or enclosed by a substrate material, including:
    a) a particulate material feeder for feeding particulate material to:
    b) a first moving endless surface with a direction of movement (MD) and with a plurality of reservoirs, said surface being adjacent said particulate material feeder, said first moving endless surface and reservoirs thereof being for receiving said particulate material from said particulate material feeder and for transferring it directly or indirectly to:
    c) a second moving endless surface, being said substrate material or being a moving endless surface carrying said substrate material, for receiving said particulate material directly or indirectly from said first moving endless surface ; and
    d) a three-dimensional plate, for applying pressure on part of said particulate material and for guiding said particulate material into said reservoirs, said plate being positioned adjacent said particulate material feeder and adjacent said first moving endless surface, said plate having a first plate face adjacent said first moving endless surface, said plate face having at least:
        i) a first surface area substantially parallel to said first moving endless surface, said first area being for applying pressure on said part of said particulate material present between said first surface area and said first moving endless surface;
        ii) a second surface area neighboring said first surface area, positioned downstream from the first surface area (in MD), said second surface area being non-parallel to said first moving endless surface and leading from said first surface area towards said first moving endless surface, said first surface area and said second surface area being connected to one another under an angle, said second surface area having an average angle with said first moving endless surface from about 10° to about 80°; and
        iii) a third surface area, neighboring said second surface area, being downstream from said second surface area (in MD), said third surface area being substantially parallel to said first moving endless surface and in closer proximity thereto than said first surface area.

2. An apparatus according to claim 1, wherein said three dimensional plate has a second plate face neighboring said first surface of said first plate face, and connected thereto with an angle from about 60° to about 120°, said second plate face optionally contacting and guiding said particulate material towards said first moving endless surface.

3. An apparatus according to claim 2, wherein said angle is from about 10° to about 80°.

4. An apparatus according to claim 1, wherein said first surface area and said second surface area have each an average length dimension (in MD) of at least about 2 mm.

5. An apparatus according to claim 1, wherein said first plate face has a width substantially equal to the width of said first moving endless surface.

6. An apparatus according to claim 1, wherein said first moving endless surface is a first rotating drum with a surface comprising said reservoirs, said drum having a drum radius, and wherein said first surface area of said first plate face is curved having a curvature with a plate face radius, the ratio of said drum radius to said plate face radius being from about 8:10 to about 10:8.

7. An apparatus according to claim 6, wherein the ratio of said drum radius to said plate face radius is from about 9.5:10 to about 10:9.5.

8. An apparatus according to claim 1, wherein said three dimensional plate is connected to a pressure control means for controlling the external pressure applied by said plate on said particulate material.

9. An apparatus according to claim 8, wherein the external pressure applied by said plate on said particulate material from about 1.5 bar to about 3 bar.

10. An apparatus according to claim 8, wherein said pressure control means is capable of varying the average distance between said first surface area of said first plate face and said first moving endless surface.

11. An apparatus according to claim 8, wherein said pressure control means comprises an actuator that: (i) senses the pressure on said plate, and in response thereto, (ii) adjusts the plate position relative to said first moving endless surface, by moving of the plate towards or away from said first moving endless surface.

12. An apparatus according to claim 11, wherein said actuator senses the pressure on said first plate face, by said particulate material.

13. An apparatus according to claim 1, wherein said reservoirs have an average depth per reservoir, said depth being perpendicular to MD, from about 1.0 mm to about 8.0 mm.

14. An apparatus according to claim 13, wherein said reservoirs have an average depth per reservoir, said depth being perpendicular to MD, from about 1.5 mm to about 4.0 mm.

15. An apparatus according to claim 14, wherein said reservoirs have an average depth per reservoir, said depth being perpendicular to MD, from about 1.5 mm to about 3.0 mm.

16. An apparatus according to claim 1, wherein said particulate material feeder has an opening, to allow exit of said particulate material of the particulate material feeder to said first moving endless surface, said opening having a MD dimension from about 10 mm to about 140 mm.

17. An apparatus according to claim 16, wherein said opening has a MD dimension from about 10 mm to about 80 mm.

18. An apparatus for making a structure that comprises particulate material supported or enclosed by a substrate material, including:
   a) a particulate material feeder for feeding particulate material to:
   b) a first moving endless surface with a direction of movement (MD) and with a plurality of reservoirs, said surface being adjacent said particulate material feeder, said first moving endless surface and reservoirs thereof being for receiving said particulate material from said particulate material feeder and for transferring it directly or indirectly to:
   c) a second moving endless surface, being said substrate material or being a moving endless surface carrying said substrate material, for receiving said particulate material directly or indirectly from said first moving endless surface ; and
   d) a three-dimensional plate, for applying pressure on part of said particulate material and for guiding said particulate material into said reservoirs, said plate being positioned adjacent said particulate material feeder and adjacent said first moving endless surface, said plate having a first plate face adjacent said first moving endless surface, said plate face having at least:
      i) a first surface area substantially parallel to said first moving endless surface, said first area being for applying pressure on said part of said particulate material present between said first surface area and said first moving endless surface;
      ii) a second surface area neighboring said first surface area, positioned downstream from the first surface area (in MD), said second surface area being non-parallel to said first moving endless surface and leading from said first surface area towards said first moving endless surface, said first surface area and said second surface area being connected to one another under an angle, said second surface area having an average angle with said first moving endless surface from about 10° to about 80° ; and
   e) a pressure control means connected to said three dimensional plate for controlling the external pressure applied by said plate on said particulate material, wherein said pressure control means comprises an actuator that:
   (i) senses the pressure on said plate, and in response thereto, (ii) adjusts the plate position relative to said first moving endless surface, by moving of the plate towards or away from said first moving endless surface.

19. An apparatus according to claim 18, wherein said first plate face has a width substantially equal to the width of said first moving endless surface.

20. An apparatus according to claim 18, wherein said pressure control means is capable of varying the average distance between said first surface area of said first plate face and said first moving endless surface.

* * * * *